(12) United States Patent
Barrows

(10) Patent No.: US 7,913,326 B1
(45) Date of Patent: Mar. 29, 2011

(54) PATIENT LASER GOGGLES

(76) Inventor: Thomas D. Barrows, Maple Grove, MN (US)

( * ) Notice: Subject to any disclaimer, the term of this patent is extended or adjusted under 35 U.S.C. 154(b) by 160 days.

(21) Appl. No.: 12/455,002

(22) Filed: May 27, 2009

Related U.S. Application Data

(60) Provisional application No. 61/128,936, filed on May 27, 2008.

(51) Int. Cl.
*A61F 9/04* (2006.01)
*A61F 9/02* (2006.01)
*A61F 9/00* (2006.01)

(52) U.S. Cl. ........... 2/450; 2/426; 2/430; 2/446; 351/70; 351/77; 351/153

(58) Field of Classification Search ........... 2/6.3, 6.4, 2/6.5, 6.7, 6.8, 15, 12, 13, 426–446, 450; 351/41, 44–48, 60, 65
See application file for complete search history.

(56) References Cited

U.S. PATENT DOCUMENTS

| | | | |
|---|---|---|---|
| 2,283,752 A * | 5/1942 | Gonsett | 2/15 |
| 4,154,513 A * | 5/1979 | Goulden | 351/47 |
| 4,835,796 A | 6/1989 | Wiedner | |
| 5,390,373 A * | 2/1995 | Flory | 2/430 |
| 5,422,684 A | 6/1995 | Keller | |
| 5,894,605 A * | 4/1999 | Chiang | 2/428 |
| 5,918,600 A * | 7/1999 | Durette | 128/857 |
| 6,081,934 A * | 7/2000 | Stefanovsky et al. | 2/431 |
| 6,123,081 A * | 9/2000 | Durette | 128/858 |
| 6,234,628 B1 * | 5/2001 | Friedman | 351/48 |
| 6,371,612 B1 * | 4/2002 | Barrows | 351/48 |
| 7,188,625 B2 * | 3/2007 | Durette | 128/858 |
| 7,284,853 B2 * | 10/2007 | Friedman | 351/47 |
| 2001/0046028 A1 * | 11/2001 | Barrows | 351/48 |
| 2007/0130674 A1 * | 6/2007 | Beyer | 2/431 |

* cited by examiner

*Primary Examiner* — Bobby H Muromoto, Jr.
(74) *Attorney, Agent, or Firm* — Eggink & Eggink; Anthony G. Eggink; Katrina M. Eggink

(57) ABSTRACT

A patient laser goggle having a pair of eye cup assemblies adjustably joined to a formed bridge wire having collinear ends. Each eye cup has a clamping mechanism to which each bridge wire end is held and a strap hook to receive the looped ends of an adjustable band. The collinear bridge wire ends are horizontally and tiltably held within the clamping mechanisms so that the patient laser goggle can be easily custom fit to the eyes of a patient. Once adjusted, the clamping mechanism allows rotation of the bridge wire with respect to the eye cup so that a medical practitioner can have easy and unobstructed access to areas of the patient's face.

20 Claims, 4 Drawing Sheets

PATIENT LASER GOGGLES

This Application claims the benefit of U.S. Provisional Patent Application Ser. No. 61/128,936, filed on May 27, 2008.

BACKGROUND OF THE INVENTION

The present invention relates generally to eyewear and particularly to a laser goggle worn by a patient undergoing a medical procedure. More particularly, the present invention relates to patient laser goggles having adjustable eye cup assemblies with a removable wire bridge which is adjustably secured in clamping mechanisms which secure the bridge ends. A clamping mechanism is mounted on each eye cup to permit a medical practitioner to pivot the wire bridge without affecting the adjusted eyecup assemblies on the patient.

Various prior art eyewear structures to cover a patient's eyes have been used and proposed in the past. Eyewear goggles having fixed structures for a patient or goggles having limited nose bridge movement once adjusted for wear on the patient are known. The spring-type nose bridge wire disclosed in U.S. Pat. No. 5,918,600 to Durette, the frictionally held nose piece in U.S. Pat. No. 6,081,934 to Stefanovsky et al., and other prior art eye wear structures, all providing a pivotable nose wire, are examples of eyewear having such limited bridge movement. These frictionally and mechanically held eye shield structures have limited adjustability for patient wear and provide limited movement for the practitioner during a medical procedure. Durette U.S. Pat. No. 7,188,625 discloses an ocular surgical protective shield with eye shields having a ball/socket mounting structure mounted perpendicular to the eye shields and parallel to each other also providing a pivotable nose piece. The latter mounting structure is likewise limited in adjustability and patient eye shield comfort due to its inherently limited nose bridge movement provided to the practitioner during a medical procedure.

The eyewear of the present invention overcome these limitations and shortcomings by providing eyewear to protect the eyes of a patient from accidental exposure to a surgical laser while laser surgery or other procedures are performed in close proximity to the ocular area. The present invention provides two shields or eye cups shaped to envelop as much of the eye as possible, constructed of stainless steel, for example, to provide durability to resist the beam of the surgical laser. The eyewear provides a comfortable fit over the eye and eyelids, and allows the medical practitioner to adjust the wire bridge of the eyewear without effecting the position of the eye cups.

SUMMARY OF THE INVENTION

A patient laser goggle having a pair of eye cup assemblies adjustably joined to a formed bridge wire. Each eye cup has a clamping mechanism which provides an adjustment and connecting structure and to which each bridge wire end is held. The clamping mechanism includes a generally cylindrical housing with a cavity, a plurality of openings, a pair of guide pins and a biased and shaped push button to allow the lateral, pivotable and rotational movement of each eye cup with respect to the nose bridge structure. The collinear bridge wire ends are horizontally and tiltably held within the clamping mechanisms so that the patient laser goggle can be easily custom fit to the face and eyes of a patient. Once adjusted, the clamping structure allows rotation of the bridge wire with respect to the eye cup so that a medical practitioner can have easy and unobstructed access to areas of the patient's face.

Each eye cup is provided with a strap hook and an adjustable strap with end loops may be connected to the strap hook. Removable eye padding is provided about the periphery of each eye cup to provide patient comfort. The eye cups, clamping structures and bridge wire are preferably constructed of a non-reflective stainless steel to block or absorb laser beam or IPL (intensed pulse light) sources typically used during medical procedures.

To secure the eyewear device to the face of the patient, a hook is provided near the outside edge of each eye cup, which may be used to secure an adjustable elastic strap, for example, to be positioned around the back of the patient's head. To connect the eye cups to each other, a bridge wire is held at each end by the clamping mechanism which is fixed, i.e., welded, to its respective eye cup structure. The bridge wire center portion is shaped, for example, V-shaped, so as to allow clearance for the patient's nose, and has two straight or collinear end portions to permit adjustment of position and angle in the clamping mechanisms.

The elements of the eyewear device allow the user of the device to adjust the relative pitch angle and distance between the two eye cups to fit the patient without the need to bend the bridge wire, and also to readily permit the complete removal of the wire for the eye cups so that each may be used alone or individually. Because the ends of the wire are collinear this structure permits the V-shaped nose clearance portion of the wire to be pivoted up or down without changing the position or angle of the eye cups, allowing access to regions of the patient's nose and forehead. This action is possible without depressing the clamping device button due to the significant mechanical advantage provided between the wire and the clamp structures.

The stainless steel construction of the device elements permits cleaning and sterilization by thermal or chemical means without damage to the device, and a blasted or otherwise roughened outer surface on all components inhibits reflection of the surgical laser for additional safety.

An advantage of the patient laser goggles of the invention is to provide an easily adjustable eye cup assembly having bridge wire adjustment means which allows degrees of adjustability not taught or suggested in the prior art. Another advantage is to provide an easily and quickly assembled laser goggle structure which provides patient comfort, ease of adjustability and ease of cleaning.

These and other benefits and advantages of this invention will become clear from the following description by reference to the drawings.

DESCRIPTION OF THE PREFERRED EMBODIMENTS

Figure 1:
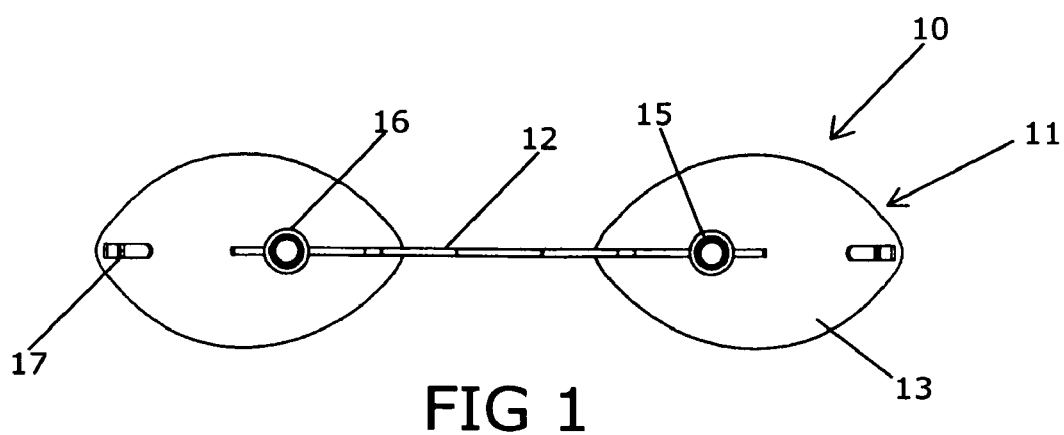
FIG. 1 is a front plan view of the patient laser goggles of the invention.
Figure 2:
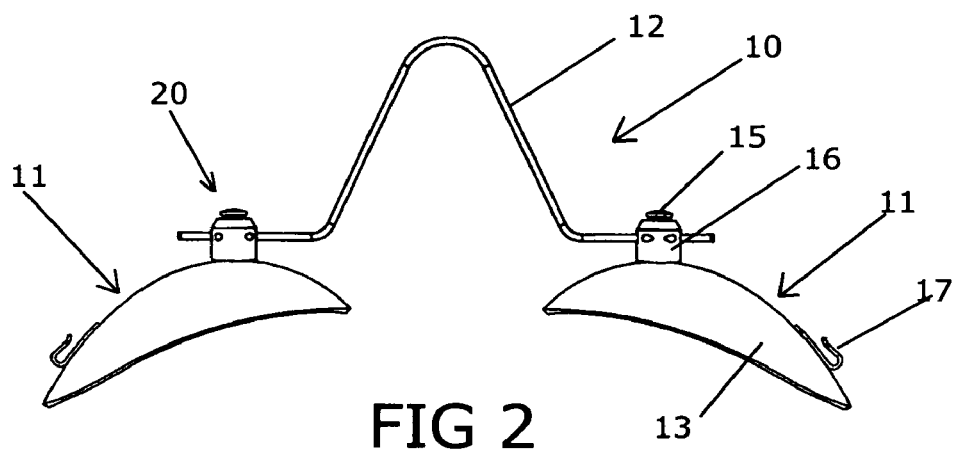
FIG. 2 is a top plan view of the goggles of FIG. 1.
Figure 3:
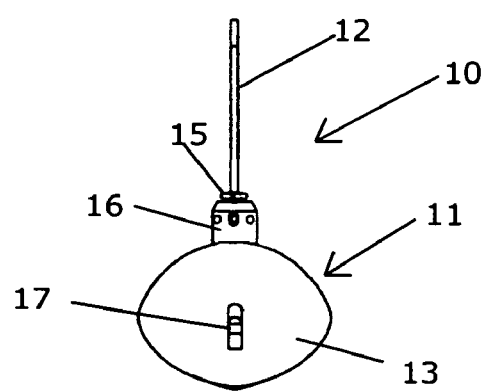
FIG. 3 is a lateral plan view of FIG. 1.
Figure 10:
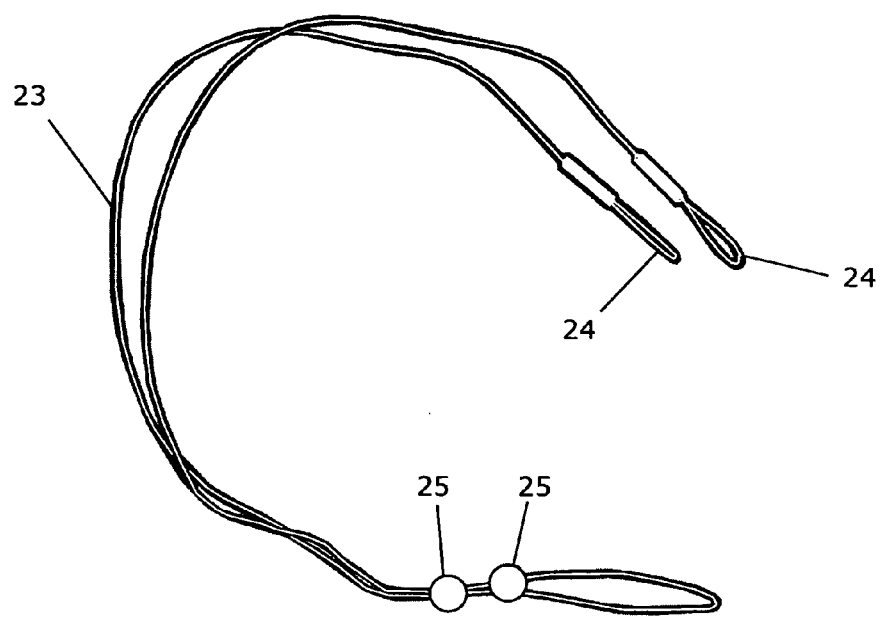
FIG. 10 is a top view of the adjustable straps of the invention.

Referring to FIGS. 1-3, the patient laser goggles 10 of the invention is shown having a pair of eye cup assemblies 11 held on the aligned end portions of a formed wire nose bridge 12. Each eye cup assembly 11 is comprised of a formed, generally oval shaped eye cup structure 13 having a bridge wire securement structure 20 formed of a generally cylindrical housing 16 and a button member 15 as further discussed below with respect to FIG. 4. Each eye cup structure 13 has an attachment hook 17 to receive an attachment loop of an adjustable strap, as shown in FIG. 10.

Figure 4:
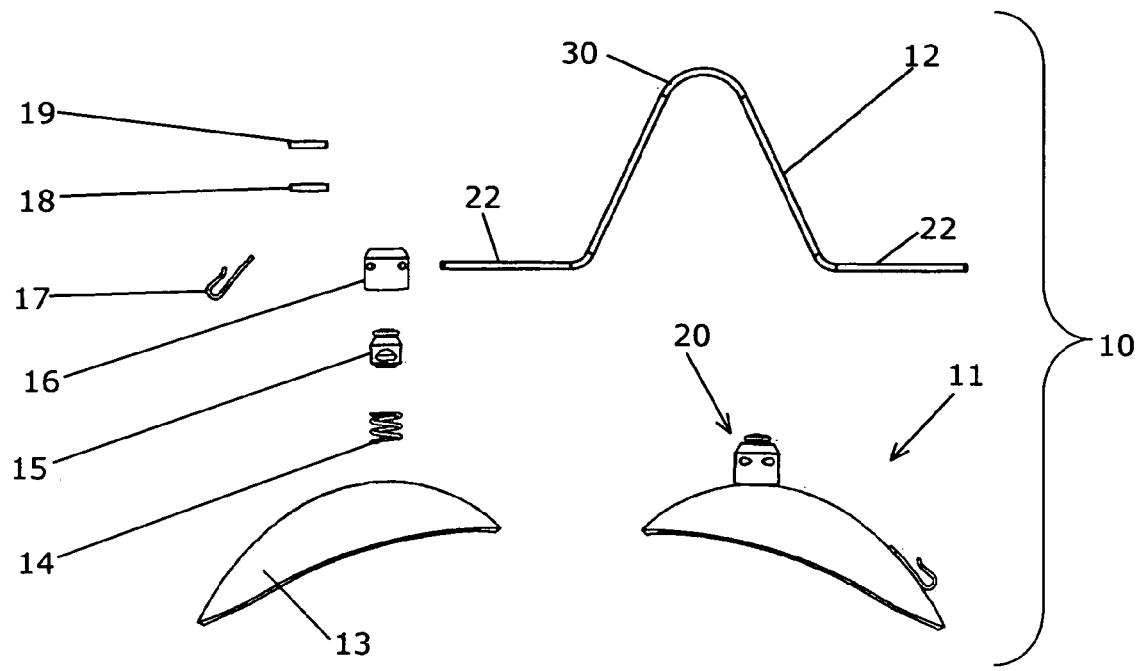
FIG. 4 shows the individual elements which cooperate to form the patient laser goggles of the invention.
Figure 5:
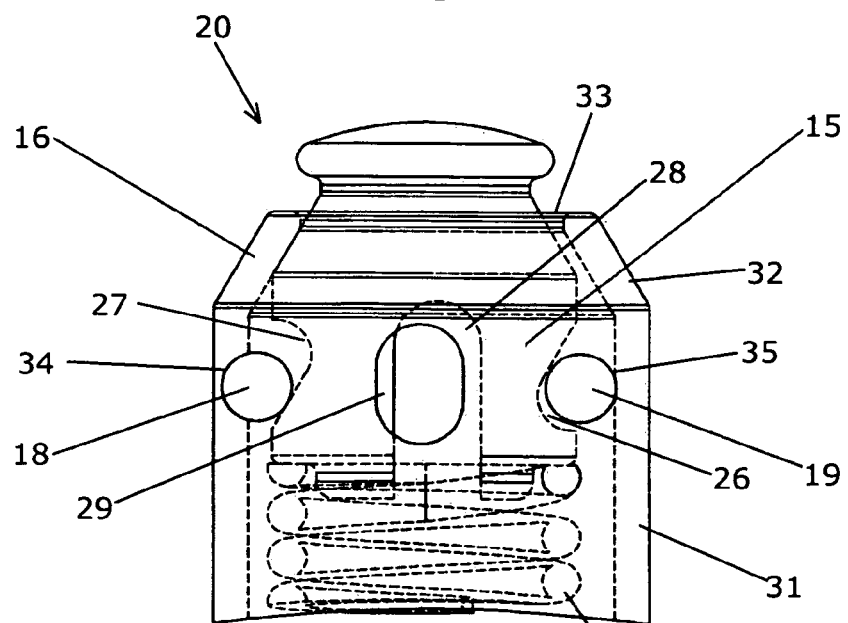
FIG. 5 is an enlarged lateral view, partially in section, showing the bridge wire mounting and adjustment structure of the invention.

FIG. 4 shows the individual elements which form the patient laser goggles 10. The clamping mechanism or bridge wire securement structure 20 is shown having a compression spring 14, a formed button member 15, a housing structure 16 and two opposing dowel or guide pins 18 and 19. As shown in FIG. 5, the formed button member 15 is smaller in dimension than the interior or cavity of housing 16 to thereby permit movement of the button 15 within the housing. The bottom of button 15 is shown having an extension to permit the button to fit into spring 14. The generally cylindrical housing 16 has peripheral wall 31 having bores 34 and 35 with the two dowel or guide pins 18 and 19 laterally positioned therein to cooperate with opposing formed indentations 26 and 27 of the button member 15. As shown, formed indentation 26 has a top rounded portion and a bottom sloped portion and formed indentation 27, on the other side of the button member 15, having a top sloped portion and a bottom rounded portion. These opposing guide pins 18, 19 in cooperation with the formed indentations 26, 27 provide means to offset the button or to allow the button to laterally move within the cavity of the housing 16.

Aligned elongated apertures 29 centrally disposed in housing 16 and central slot 28 of button member 15 allow the ends 22 of the nose bridge wire 12 to be placed therethrough when the button member 15 is depressed, due to the smaller diameter of the wire with respect to the slot and apertures. The central slot 28 is shown extending higher and lower than apertures 29. When the button member 15 is released, the cooperating movement of the offset curved formed indentations 26 and 27 with respect to the fixed guide pins 18 and 19 cause the central slot 28 in the button member 15 to move laterally to thereby pinch or secure the bridge wire ends 22. This button member 15 movement allows the bridge wire ends 22 to be adjusted with respect to the housing 16 and thus the eye cup 13 to which the housing 16 is mounted. For example, the pitch angle of each eye cup is easily adjusted on the bridge wire ends and, upon depressing button member 15, the width of the goggles or the distance between the eye cups is easily laterally adjusted on the bridge wire ends 22.

In summary, each clamping mechanism 20 comprises essentially of three cooperating elements, namely the cylindrical housing 16, the formed button member 15 and the spring 14 or other biasing means. The clamping mechanism 20 acts on the end 22 of the wire 12 by pinching it to prevent motion, or releasing it to permit motion. The housing 16, through which the end 22 of the wire passes, has two generally oval openings 29 which permit the wire to pivot or pitch up and down relative to the eye cup 13. The end 22 of the wire may also be free to spin or rotate about its axis in oval openings 29 and to slide along its length. The button member 15 has a similar central slot 28 which permits a change of pitch angle. The compression spring 14 pushes the button toward the top opening 33 of the housing 16, where conical seat or shoulder 32 and two guide pins 18 and 19 ramp the button member 15 toward one side, thereby pinching the end of the wire between the slot 28 of the button member 15 and the openings 29 of the housing. The action of depressing the button, in compressing the spring and moving the button member 15 away from the conical seat 32 of the housing 16, will permit the button to move laterally to allow clearance for the end of the wire 22 for adjustment.

Figure 6A:
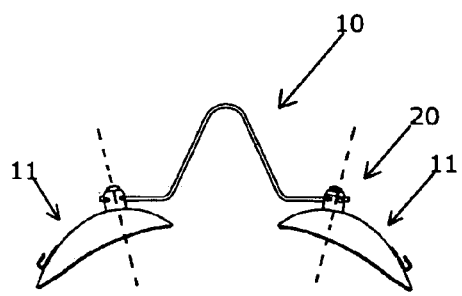
FIGS. 6a and 6b are top views showing an adjusted position of the eye cup assemblies with respect to the bridge wire.
Figure 6B:
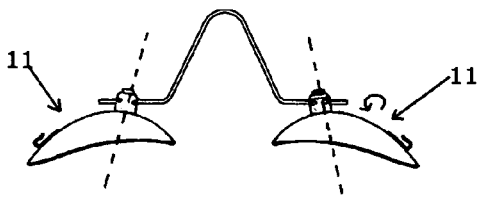

FIGS. 6a and 6b show the eye cup assembly 11 to be tilted or placed in a pitched position with respect to the bridge wire ends 22. Specifically, FIGS. 6a and 6b show two opposite positions, for example, with the eye cups 13 tilted inwardly and outwardly, respectively, as shown by the dotted line axis intersecting the bridge wire securement structures 20.

Figure 7A:
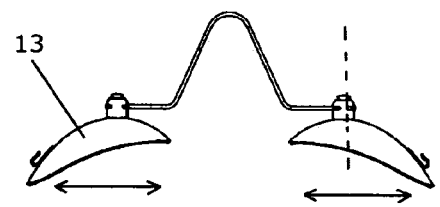
FIGS. 7a and 7b are top views showing the eye cup assemblies adjusted having another pitch or tilted position.
Figure 7B:
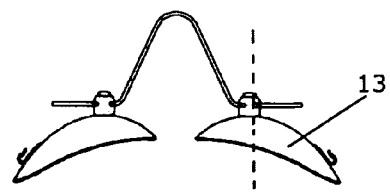

FIGS. 7a and 7b show the lateral movement positions of the eye cups 13 with respect to the nose bridge wire ends. FIG. 7a shows the eye cups positioned at the ends of the wire nose bridge and FIG. 7b shows the eye cups moved inwardly adjacent the centrally disposed hook bend of the wire bridge. The dotted axis indicates that the eye cups are not tilted with respect thereto.

Figure 8:
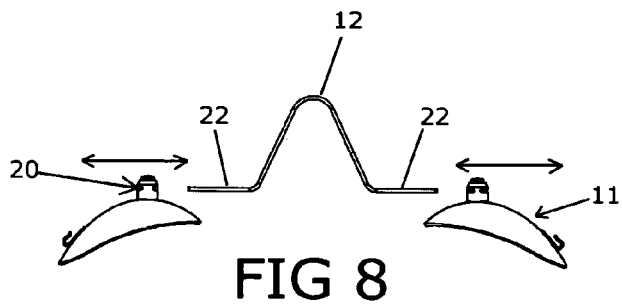
FIG. 8 is a top view of the bridge wire and eye cup assemblies in a separated state.

FIG. 8 shows the eye cups 11 removed from the bridge wire 12. The ability for easy removal by suppressing the button 15 of clamping mechanism 20 allows the components of the eye goggle to be easily cleaned, via an autoclave for example. Further, the eye cups 13 may be utilized during a medical procedure without the use of the nose bridge 12. The easily assembling and disassembling eyewear structure of this invention provides numerous benefits.

Figure 9:
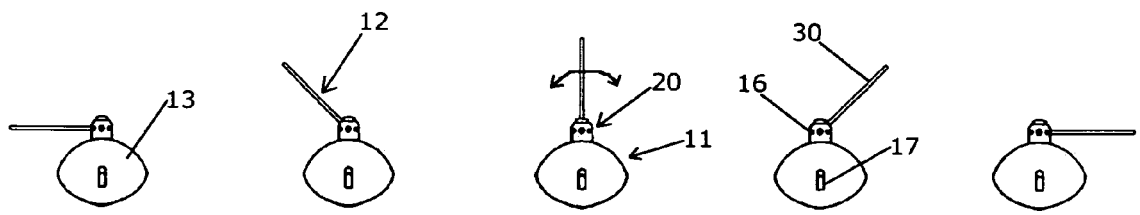
FIG. 9 are lateral views showing various rotationally adjusted positions of the eye bridge with respect to an eye cup assembly.

FIG. 9 shows a sequence of the eye cup 13 being in a stationary position and showing the generally V-shaped center portion 30 of the wire nose bridge being rotated with respect to housing 16. Thus, subsequent the fitting of the eyewear to the face of a patient, the mounting structure 20 permits a smooth and easy rotational movement of the nose bridge 12 as preferred during a medical procedure.

FIG. 10 shows the adjustable strap 23 having loop attachment portions 24 for attachment to hooks 17. The strap may be adjustable and is shown having an annular sliding member(s) 25 for strap length adjustment. Two straps may be provided with the assembly, one strap may be white, the other black, thereby providing a choice for the practitioner. For example, black straps may be more susceptible to damage than white straps when contacted by certain laser beams.

Figure 11:
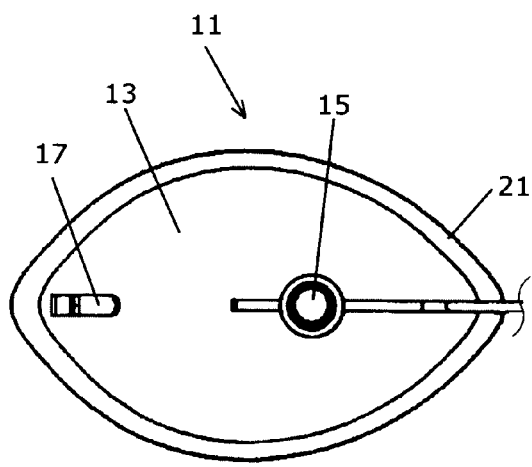
FIG. 11 is a front plan view of an eye cup assembly of the invention having eye padding attached about the cup periphery.
Figure 12:
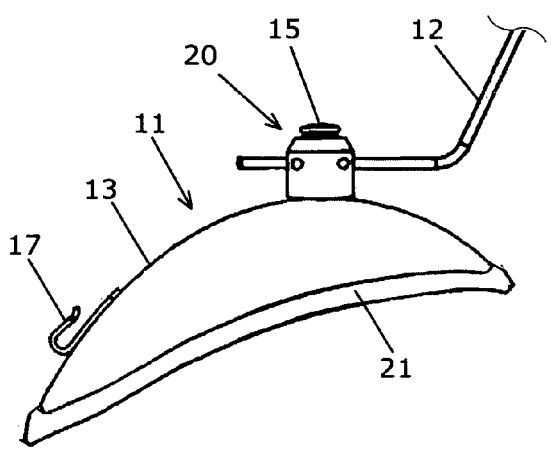
FIG. 12 is a top plan view of the eye cup assembly and eye padding of FIG. 11.

FIGS. 11 and 12 show the eye cup 13 of the eye goggles assembly having peripheral padding 21 around the cup periphery. The eye goggles assembly may be utilized with or without the peripheral pads which are provided for patient comfort. The eye pads 21 are shown to be thin oval rings that may be applied to and frictionally held on the outer peripheral edge of the stainless steel eye cups for patient comfort.

The eye cups 13, bridge wire 12, and the housing 16, compression spring 14, button member 15, strap hooks 17 and dowel or guide pins 18 and 19 are preferably constructed of medical grade stainless steel or the like. This stainless steel composition has been shown to provide a suitable composition for use with all types of laser sources as well as intensed pulsed light (IPL) sources. The straps may be formed of a flexible elastic structure, for example, and the eye pads are preferably formed of a medical grade white silicone composition. The eye pads 21 are easily attached and removed from the eye cup and are provided for patient comfort.

As many changes are possible to the patient laser goggles of this invention utilizing the teachings thereof, the descriptions above and the accompanying drawings should be interpreted in the illustrative and not in the limited sense.

That which is claimed is:

1. A patient laser goggle comprising:
    a) a pair of eye cup assemblies, each having an oval-cup-shaped eye cup with a strap hook and a clamping mechanism mounted thereto;
    b) said clamping mechanism having a generally cylindrical housing mounted to said eye cup, said housing having a cavity, a biased button member positioned for movement in said cavity, and a plurality of openings therethrough, said openings including a pair of aligned generally oval openings each having a predetermined width and means to offset said biased button in said cavity;
    c) a formed bridge wire having ends for insertion through said aligned oval openings of said clamping mechanism housing, said bridge wire ends having a diameter smaller that said width of said generally oval openings in said generally cylindrical housing; and
    d) an adjustable strap for attachment to said strap hooks.

2. The patient laser goggle of claim 1, wherein said housing of said clamping mechanism has a peripheral wall, a cylindrical shoulder and a top opening, and wherein said means to offset said biased button includes aligned outside openings through said peripheral wall of said housing for receiving and fixing a pair of guide pins in said housing.

3. The patient laser goggle of claim 2, wherein said biased button includes a compression spring, said button being positioned above said spring and extending through said top opening.

4. The patient laser goggle of claim 3, wherein a pair of guide pins are fixed in said aligned outside openings and wherein said button has opposing, offset curved indentations which cooperate with said pair of guide pins to laterally move said button in said housing when said button is depressed.

5. The patient laser goggle of claim 1, wherein a peripheral padding is provided on the perimeter of each eye cup for patient comfort.

6. The patient laser goggle of claim 1, wherein said eye cup assembly is constructed of medical grade stainless steel.

7. The patient laser goggle of claim 3, wherein said formed bridge wire includes a generally V-shaped mid-portion.

8. The patient laser goggle of claim 6, wherein each said eye cup has a non-reflective surface.

9. A patient laser goggle comprising:
    a) a pair of eye cups each having a strap hook;
    b) a formed wire nose bridge member having a generally V-shaped middle portion and two collinear end portions; and
    c) a clamping mechanism mounted on each said eye cup, said clamping mechanism having a generally cylindrical housing member with a compression spring disposed therein and a depressible button on said compression spring and extending upwardly therefrom, said housing member having generally opposing centrally disposed apertures and means to secure a pair of dowel pins, said depressible button having a central slot and offset opposing curved indentations, each said wire end of said formed wire nose bridge being constructed to extend through said opposing central apertures in said housing member and said central slot of said button, and said secured dowel pins being constructed and arranged to engage said opposing indentations of said button to allow three-dimensional movement of said collinear end portions in said clamping mechanisms.

10. The patient laser goggle of claim 9, wherein peripheral eye padding is provided for mounting around the periphery of each said eye cup.

11. The patient laser goggle of claim 9, wherein said eye cups, formed wire nose bridge, housing, compression spring, button, strap hooks and dowel pins are constructed of a medical grade stainless steel composition.

12. The patient laser goggle of claim 9, wherein an adjustable strap is provided having end loops for attachment to each said eye cup strap hook.

13. The patient laser goggle of claim 9, wherein said three-dimensional movement of said collinear formed wire end portions includes sliding said end portion with respect to said clamping mechanism and eye cup, rotating said end portion within said clamping mechanism and pivoting said end portion with respect to said clamping mechanism and eye cup.

14. The patient laser goggle of claim 11, wherein each said eye cup has a non-reflective surface.

15. An adjustable patient laser goggle comprising:
    a) a pair of eye cup assemblies, each eye cup assembly having an eye cup, strap attachment means and a clamping mechanism mounted thereto,
    b) said clamping mechanism having a generally cylindrical housing with a wall, a plurality of openings including a top opening and a pair of aligned opposing openings through said wall of said cylindrical housing,
    c) said generally cylindrical housing further having a cavity and having a compressible spring in said cavity and a push button communicating with said compressible spring and extending from said housing through said top opening,
    d) a formed bridge wire having generally collinear ends for extension through said aligned openings of each said housing; and
    e) an adjustable strap for attachment to said strap attachment means of said eye cup assemblies whereby each said eyecup assembly is adjustable in the x, y, z direction with respect to said collinear end of said formed bridge wire, whereby upon the adjustable positioning of each said eyecup assembly with respect to the eye of a patient, said formed bridge is rotatable with respect to each said clamping mechanism to provide unobstructed access to the face of a patient without affecting the position of said eye assemblies with respect to the eyes of the patient.

16. The adjustable patient laser goggle of claim 15, wherein each said push button member has opposing formed lateral surfaces offset with respect to each other and wherein a pair of opposing guide pins are provided in said cavity of each said housing for engagement with said opposing formed lateral surfaces of said push button.

17. The adjustable patient laser goggle of claim 15, wherein a peripheral padding member is provided for each said eye cup.

18. The adjustable patient laser goggle of claim 15, wherein said formed bridge wire has a generally V-shaped structure between said collinear ends.

19. The adjustable patient laser goggle of claim 18, wherein said peripheral padding is formed of silicone and wherein said eyecup, bridge wire and clamping mechanism are constructed of stainless steel.

20. The patient laser goggle of claim 19, wherein each said eye cup has a non-reflective surface.

* * * * *